(12) United States Patent
Thomas et al.

(10) Patent No.: US 8,409,511 B2
(45) Date of Patent: Apr. 2, 2013

(54) ORGANIC CHEMICAL SENSOR WITH MICROPOROUS ORGANISILICATE MATERIAL

(75) Inventors: John Christopher Thomas, St. Paul, MN (US); Neal A. Rakow, Woodbury, MN (US); Michael S. Wendland, St. Paul, MN (US); Stefan H. Gryska, Woodbury, MN (US); Michael C. Palazzotto, Woodbury, MN (US); John E. Trend, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 13/141,585

(22) PCT Filed: Dec. 22, 2009

(86) PCT No.: PCT/US2009/069105
§ 371 (c)(1),
(2), (4) Date: Jun. 22, 2011

(87) PCT Pub. No.: WO2010/075333
PCT Pub. Date: Jul. 1, 2010

(65) Prior Publication Data
US 2011/0254568 A1 Oct. 20, 2011

Related U.S. Application Data

(60) Provisional application No. 61/140,141, filed on Dec. 23, 2008.

(51) Int. Cl.
*G01N 27/00* (2006.01)

(52) U.S. Cl. .............. 422/98; 422/88; 422/90; 324/663; 361/280; 361/305; 361/311

(58) Field of Classification Search .................. None
See application file for complete search history.

(56) References Cited

U.S. PATENT DOCUMENTS

| | | | |
|---|---|---|---|
| 5,143,696 | A | 9/1992 | Haas |
| 5,304,363 | A | 4/1994 | Beck |
| 5,828,542 | A | 10/1998 | Riley |
| 5,857,250 | A | 1/1999 | Riley |
| 5,858,457 | A | 1/1999 | Brinker |
| 5,861,545 | A | 1/1999 | Wood |

(Continued)

FOREIGN PATENT DOCUMENTS

| | | |
|---|---|---|
| JP | 06-281610 | * 10/1993 |
| KR | 10-1997-0011025 | 7/1997 |

(Continued)

OTHER PUBLICATIONS

Nagai, K., et al. Poly[1-(trimethylsilyl)-1-propyne] and related polymers: synthesis, proprties and functions, 2001, Progress in Polymer Science, vol. 26, pp. 721-798.*

(Continued)

*Primary Examiner* — Robert Xu
(74) *Attorney, Agent, or Firm* — Jeffrey M. Olofson (57) ABSTRACT

Sensing elements for sensing organic chemical analytes are disclosed. The sensing elements include a first electrode and a second electrode, and a substantially microporous, amorphous, hydrophobic, analyte-responsive organosilicate material in proximity to the first and second electrodes.

14 Claims, 4 Drawing Sheets

U.S. PATENT DOCUMENTS

| | | | |
|---|---|---|---|
| 5,877,895 A | 3/1999 | Shaw | |
| 5,922,299 A | 7/1999 | Bruinsma | |
| 6,180,318 B1 | 1/2001 | Fitzer | |
| 6,248,686 B1 | 6/2001 | Inagaki | |
| 6,270,846 B1 | 8/2001 | Brinker | |
| 6,326,326 B1 | 12/2001 | Feng | |
| 6,329,017 B1 | 12/2001 | Liu | |
| 6,365,266 B1 | 4/2002 | MacDougall | |
| 6,387,453 B1 | 5/2002 | Brinker | |
| 6,396,616 B1 | 5/2002 | Fitzer | |
| 6,566,243 B2 | 5/2003 | Gaynor | |
| 6,592,980 B1 | 7/2003 | MacDougall | |
| 6,630,696 B2 | 10/2003 | Yan | |
| 6,664,071 B1 | 12/2003 | Windhab | |
| 6,696,258 B1 | 2/2004 | Wei | |
| 6,713,643 B2 | 3/2004 | Pinnavaia | |
| 6,818,289 B2 | 11/2004 | Weigel | |
| 6,882,165 B2 | 4/2005 | Ogura | |
| 6,942,918 B2 | 9/2005 | MacDougall | |
| 7,067,687 B2 | 6/2006 | Pinnavaia | |
| 7,109,130 B2 | 9/2006 | Davis | |
| 7,141,859 B2 | 11/2006 | DeBoer | |
| 7,153,355 B2 | 12/2006 | Sakamoto | |
| 7,307,343 B2 | 12/2007 | Kirner | |
| 2004/0184948 A1 | 9/2004 | Rakow | |
| 2005/0258578 A1 | 11/2005 | Birnbaum | |
| 2005/0282401 A1 | 12/2005 | Davis | |
| 2006/0009575 A1 | 1/2006 | Nakashima | |
| 2006/0032312 A1 | 2/2006 | Auner | |
| 2006/0046079 A1 | 3/2006 | Lee | |
| 2006/0063178 A1 | 3/2006 | Rauh-Adelmann | |
| 2006/0084277 A1 | 4/2006 | Nakashima | |
| 2006/0110940 A1 | 5/2006 | Seon | |
| 2006/0145306 A1 | 7/2006 | Lee | |
| 2006/0159938 A1 | 7/2006 | Lee | |
| 2006/0246273 A1* | 11/2006 | McKeown et al. | 428/314.8 |
| 2007/0129613 A1 | 6/2007 | Rochester | |
| 2007/0184557 A1 | 8/2007 | Crudden | |
| 2008/0006375 A1 | 1/2008 | Meadows | |
| 2011/0257281 A1 | 10/2011 | Thomas | |

FOREIGN PATENT DOCUMENTS

| | | |
|---|---|---|
| KR | 10-0373210 | 2/2003 |
| KR | 10-2003-0086637 | 11/2003 |
| KR | 10-2007-0098414 | 10/2007 |
| WO | WO 1994-028372 | 12/1994 |
| WO | WO 2010-075014 | 7/2010 |
| WO | WO 2010-075328 | 7/2010 |

OTHER PUBLICATIONS

Gerwen, P. V., et al. Nanoscaled interdigitated electrode arrays for biochemical sensors, 1998, Sensors and Actuators B, vol. 49, pp. 73-80.*

Walcarius, A. et al., Exciting new directions in t eintersection of functionalized sol-gel material with electrochemistry, 2005, Journal of Material Chemistry, vol. 15, pp. 3663-3689.*

Nelson, "Gas Mixtures: Preparation and Control", Lewis Publishers, 1992, Title, Publication and Table of Contents, 6 pgs.

International Search Report for PCT/US2009/069099, mailed Jul. 13, 2010, 3 pages.

International Search Report for PCT/US2009/067804, mailed Aug. 16, 2010, 3 pages.

International Search Report for PCT/US2009/069105, mailed Jul. 26 2010, 3 pages.

* cited by examiner

ORGANIC CHEMICAL SENSOR WITH MICROPOROUS ORGANISILICATE MATERIAL

CROSS REFERENCE TO RELATED APPLICATIONS

This application is a national stage filing under 35 U.S.C. 371 of PCT/US2009/069105, filed Dec. 22, 2009, which claims priority to U.S. Provisional Application No. 61/140,141, filed Dec. 23, 2008, the disclosure of which is incorporated by reference in its/their entirety herein.

FIELD OF THE DISCLOSURE

The disclosure relates to sensors and sensing elements, including sensing elements which are suitable for detecting or monitoring organic chemical analytes in an environment. The sensors and sensing elements include microporous organosilicate materials.

BACKGROUND

The ability to detect chemical analytes, especially organic chemical analytes, is important in many applications, including environmental monitoring, and the like. Such detection and/or monitoring of organic molecules may find particular use in, for example, so called End of Service Life Indicators which are desired for personal protective equipment such as respirators.

Many methods for the detection of chemical analytes have been developed, for example optical, gravimetric, microelectromechanical, and so on. In particular, sensors that monitor electrical properties such as capacitance, impedance, resistance, etc., have been developed. Often, such sensors rely on the change that occurs in the electrical properties of a material upon adsorption of an analyte onto, or absorption of an analyte into, the material.

SUMMARY

The present disclosure includes sensing elements for sensing an organic chemical analyte, comprising a first electrode and a second electrode, and a microporous, hydrophobic, analyte-responsive organosilicate material disposed at least in proximity to the first and second electrodes. The microporous organosilicate material defines a pore volume. The pore volume is microporous, with at least 50% of the pore volume comprising pores with a diameter of less than 2 nanometers.

Also disclosed are methods of sensing organic chemical analytes. These methods include providing a sensor that comprises a sensing element that comprises a first electrode and a second electrode and a substantially microporous, amorphous, hydrophobic, analyte-responsive organosilicate material disposed at least in proximity to the first and second electrodes, wherein the substantially microporous, amorphous, hydrophobic, analyte-responsive organosilicate material comprises micropores which define a pore volume, and, an operating circuit in electrical communication with the first and second electrodes, wherein the operating circuit is capable of applying a voltage to the first and second electrodes and is capable of detecting a change in an electrical property of the sensing element, exposing the sensing element to an environment potentially containing one or more organic chemical analytes, applying a voltage to the first and second electrodes, and monitoring an electrical property of the sensing element. In some embodiments the electrical property monitored is a capacitive property.

Like reference symbols in the various figures indicate like elements. Unless otherwise indicated, all figures and drawings in this document are not to scale and are chosen for the purpose of illustrating different embodiments. In particular, the dimensions of the various components are depicted in illustrative terms only, and no relationship between the dimensions of the various components should be inferred from the drawings.

DETAILED DESCRIPTION

The present disclosure includes sensing elements for sensing an organic chemical analyte, comprising a first electrode and a second electrode, and a microporous, hydrophobic, analyte-responsive organosilicate material disposed at least in proximity to the first and second electrodes.

The terms "capacitance" and "capacitance-related property" encompass any electrical property and the measurement thereof that is in general associated with the imparting of an electrical charge (whether static or time variant) and the monitoring of an electrical property during and/or after the imparting of the charge. Such properties include not only capacitance, but also impedance, admittance, resistance, conductance, etc., and may be measured according to various methods known in the art.

Figure 1:
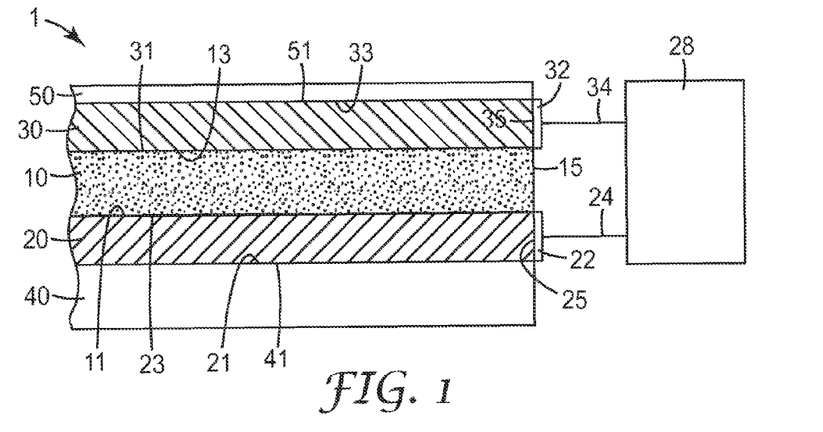
FIG. 1 is a side view of an exemplary sensing element in a parallel-plate configuration.
Figure 2:
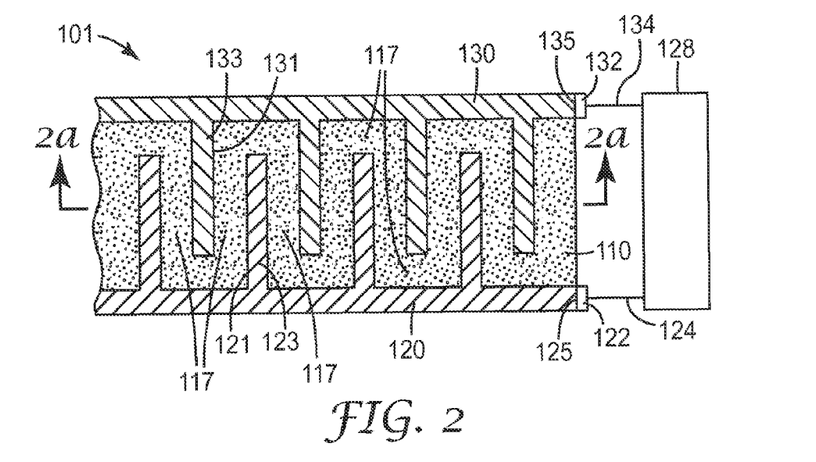
FIG. 2 is a top view of an exemplary sensing element in an interdigitated configuration.

In this context, the terms "microporous" and "microporosity" mean that the material has a significant amount of internal, interconnected pore volume, with the mean pore diameter being less than about 2 nm. Such microporosity provides that molecules of organic analyte (if present) will be able to penetrate the internal pore volume of the material and take up residence in the internal pores. The presence of such analyte in the internal pores can alter the dielectric properties of the material such that a change in the dielectric constant (or any other suitable electrical property) can be observed. Without being limited by theory or mechanism, applicant considers that the disclosed sensing element 1/101, relying on a microporous organosilicate material, may have advantageous properties with regard to the sensing of an organic analyte, in that a measurable change in an electrical property of the dielectric material may be caused by the presence of the analyte molecules in the pores. Such a microporous nature of the analyte-responsive organosilicate material may contribute to increased sensitivity of the dielectric material to small amounts of organic analyte.

In this context, the term "analyte-responsive material" means a material that is capable of adsorbing an organic chemical analyte, and that can exhibit a measurable change in some electrical property of the material upon absorbing the organic analyte into the material.

As used herein, the term "microporous" refers to porous materials that have average pore diameter sizes less than about 2 nanometers.

As used herein, the term "hydrophobic" refers to compositions which do not attract water. The hydrophobic nature of compositions may be measured in a variety of ways, including by the adsorption of water over a given period of time at a given relative humidity.

As used herein, the term "amorphous" refers to compositions which are substantially non-crystalline. Typically when scanned with a X-ray diffractometer the compositions do not show a discernable X-ray diffraction pattern when scanned from 0.5 to 80 degrees (2θ).

As used herein, the term "organosilicate" refers to compositions that are hybrids containing a covalently linked three dimensional silica network (—Si—O—Si—) with some organo-functional groups R, where R is a hydrocarbon or heteroatom substituted hydrocarbon group linked to the silica network by at least one Si—C bond.

As used herein, the term "hydrocarbon group" refers to a group which contains carbon and hydrogen bonds. A hydrocarbon group may be linear, branched, cyclic, or aromatic. Examples of hydrocarbon groups are alkyl groups and aryl groups.

As used herein, the term "substituted hydrocarbon group" is a hydrocarbon group which contains one or more heteroatoms, such as oxygen, nitrogen, sulfur, phosphorous, boron, a halogen (F, Cl, Br, or I), arsenic, tin or lead. The heteroatoms may be pendant or catenary.

As used herein, the term "alkyl" refers to a monovalent group that is a radical of an alkane, which is a saturated hydrocarbon. The alkyl can be linear, branched, cyclic, or combinations thereof and typically has 1 to 20 carbon atoms. In some embodiments, the alkyl group contains 1 to 18, 1 to 12, 1 to 10, 1 to 8, 1 to 6, or 1 to 4 carbon atoms. Examples of alkyl groups include, but are not limited to, methyl, ethyl, n-propyl, isopropyl, n-butyl, isobutyl, tert-butyl, n-pentyl, n-hexyl, cyclohexyl, n-heptyl, n-octyl, and ethylhexyl.

As used herein, the term "aryl" refers to a monovalent group that is aromatic and carbocyclic. The aryl can have one to five rings that are connected to or fused to the aromatic ring. The other ring structures can be aromatic, non-aromatic, or combinations thereof. Examples of aryl groups include, but are not limited to, phenyl, biphenyl, terphenyl, anthryl, naphthyl, acenaphthyl, anthraquinonyl, phenanthryl, anthracenyl, pyrenyl, perylenyl, and fluorenyl.

As used herein, the term "alkylene" refers to a divalent group that is a radical of an alkane. The alkylene can be straight-chained, branched, cyclic, or combinations thereof. The alkylene often has 1 to 20 carbon atoms. In some embodiments, the alkylene contains 1 to 18, 1 to 12, 1 to 10, 1 to 8, 1 to 6, or 1 to 4 carbon atoms. The radical centers of the alkylene can be on the same carbon atom (i.e., an alkylidene) or on different carbon atoms.

As used herein, the term "arylene" refers to a divalent group that is carbocyclic and aromatic. The group has one to five rings that are connected, fused, or combinations thereof. The other rings can be aromatic, non-aromatic, or combinations thereof. In some embodiments, the arylene group has up to 5 rings, up to 4 rings, up to 3 rings, up to 2 rings, or one aromatic ring. For example, the arylene group can be phenylene.

As used herein, the term "aralkylene" refers to a divalent group of formula —$R^a$—$Ar^a$— where $R^a$ is an alkylene and $Ar^a$ is an arylene (i.e., an alkylene is bonded to an arylene).

As used herein, the term "alkoxy" refers to a group of the formula —OR, where R is an alkyl, aryl, or substituted alkyl group.

As used herein, the term "acetoxy" refers to a group of the formula —OC(O)CH$_3$, where C(O) refers to a carbonyl group C=O.

As used herein, the term "amino" refers to a groups of the formula —NR$_2$, where R is an alkyl, aryl, or substituted alkyl group.

As used herein, the term "pore size" refers to the diameter of a pore and the term "pore volume" refers to the volume of a pore.

As used herein, the term "porogen" refers to a material that facilitates the formation of a porous structure. Solvents typically are not considered to be porogens in this context.

As used herein, the terms "calcine" and "calcination" refers to heating a mixture, such as a sol, to a temperature below the melting point to drive off volatile materials and form an organosilicate network.

As used herein, the term "sol" refers to a precursor mixture containing reactive organosilicate materials in a solvent that forms a continuous organosilicate network upon calcination.

With reference to FIGS. 1 and 2, herein is disclosed a sensing element 1/101 that comprises at least an analyte-responsive organosilicate layer 10/110 in proximity to a first electrode 20/120 and a second electrode 30/130. These components, and features and properties thereof, as well as other optional components and the features and properties thereof, will be discussed in turn. These discussions will refer to both FIG. 1, which depicts an exemplary sensing element based on the general configuration of a parallel-plate capacitor, and FIGS. 2, 2a, and 3, which depict exemplary sensing elements based on the general configuration of an interdigitated capacitor. For clarity, the various components have been given different reference numbers (generally, incremented by 100) in the Figs. depicting the different general configurations. However, it should be understood that the structure, composition and properties of the various components, may be applicable to sensing elements of any capacitive design, unless otherwise stated.

The sensing element 1/101 is configured such that the analyte-responsive organosilicate layer 10/110 is in sufficiently close proximity to the first electrode 20/120 and the second electrode 30/130 that the analyte-responsive organosilicate material contained in the layer will be capable of interacting with an electric field that is established by the electrodes. In operation of sensing element 1/101, analyte-responsive organosilicate layer 10/110 exhibits a change in an electrical property upon absorption of one or more analytes. In one embodiment, the electrical property is capacitance or a capacitance-related property as described below. Such a change in a capacitance-related property can be measured by imparting a charge differential between the first electrode 20/120 and the second electrode 30/130 (e.g., by imparting a voltage differential to the electrodes) and monitoring the property of the sensing element in response to the presence of the analyte. Such monitoring can be done by the use of an operating circuit 28/128, as described later herein.

The analyte-responsive organosilicate layer 10/110 (the term "layer" being used generically and encompassing any physical configuration) comprises at least in part an amorphous, microporous, hydrophobic, analyte-responsive organosilicate material.

Organosilicate compositions are hybrid compositions that contain a silica framework as well as organo-functional groups. The organosilicate compositions comprise $RSiO_3$ units linked through bridging Si—O—Si linkages, where R may be a hydrocarbon group or substituted hydrocarbon group. The R group is bonded to the silica matrix by a covalent Si—C bond.

The organosilicate compositions of this disclosure may be described as having a relatively high organic content. The relatively high organic content of the organosilicate compositions is a desirable feature because, as is discussed below, it affects the hydrophobicity of the organosilicate compositions. The relatively high organic content may be achieved in a number of ways. For example, there may be many $RSiO_3$ units present with R being relatively small hydrocarbon groups such as methyl, ethyl, propyl, etc. to give a high organic content or there may be fewer $RSiO_3$ units with R being relatively large hydrocarbon groups such as aryl.

A wide variety of organo-functional groups (R groups in the $RSiO_3$ units) are suitable for use in the organosilicate compositions. The organo-functional groups may be simple alkyl or alkylene groups such as methyl, ethyl, propyl, methylene, ethylene, propylene, and the like or more complex alkyl or alkylene groups. The organo-functional groups may also be aromatic groups such as aryl, substituted aryl or the like. In some embodiments, the R group may be alkylene or arylene group that links two $SiO_3$ units (e.g. —$O_3Si$—R—$SiO_3$—). Examples of suitable aryl and arylene groups include, for example, phenyl, tolyl, naphthyl, phenylene, tolylene, bisphenylene, and the like.

In some embodiments, the organosilicate compositions may contain at least some aromatic content (i.e. aryl and/or arylene groups). Arylene groups, where the arylene group is linked to 2 silicon atoms, are particularly suitable because it is believed that the rigid aromatic rings help to provide the desirable pore structure. Among the particularly suitable aryl and arylene groups are phenyl, naphthyl, and bisphenylene.

The organo-functional nature of the organosilicates tend to render the compositions hydrophobic, since organic groups are naturally oleophilic (literally "oil loving") and are more compatible with other organo-functional species than with water. The hydrophobic nature of the compositions makes these materials less likely to adsorb moisture from the atmosphere. The adsorption of moisture from the atmosphere is undesirable, especially in instances where these materials are utilized in sensor applications where sensing of organic molecules is desired. If the pores were to substantially adsorb moisture from the environment, the ability of the pores to adsorb organic analytes of interest would be diminished. However, since the compositions are hydrophobic, this renders them relatively unaffected by moisture from the environment.

Hydrophobicity can be measured in a variety of ways. One technique that is particularly useful is to expose the hydrophobic, amorphous, substantially microporous, organosilicate compositions to an environment with a given relative humidity, such as 50% relative humidity at room temperature, for a sufficient period of time such that the adsorbed water and water in the atmosphere are at equilibrium. This equilibrium state can be determined by plotting a graph of time versus adsorption and observing where the profile curve plateaus. In some embodiments of this disclosure, the film adsorbs water into less than 50% of the available pore volume at a relative humidity of 50% at equilibrium. In some embodiments the film adsorbs water into less than 30% of the available pore volume at a relative humidity of 50% at equilibrium.

The organosilicate compositions are amorphous or substantially amorphous, meaning that they are free or essentially free of crystallinity. While not wishing to be bound by theory, it is believed that amorphous organosilicates contain more diverse porous structures making them suitable for a wide range of analytes in, for example, sensing applications.

The amorphous nature of the organosilicate compositions can be determined, for example, through the use of an X-ray diffractometer. Typically, when scanned with a X-ray diffractometer, the compositions do not show a discernable X-ray diffraction pattern when scanned from 0.5 to 80 degrees ($2\theta$). By no discernable X-ray diffraction pattern it is meant that X-ray diffraction data are essentially featureless, indicating no evidence for the presence of structural order.

The organosilicate compositions are substantially microporous. Porous materials have been classified in many different ways. The IUPAC definitions for porous materials define porous materials with an average pore diameter of less than 2 nanometers as microporous, porous materials with an average pore diameter of from 2-50 nanometers as mesoporous, and porous materials with an average pore diameter of greater than 50 nanometers as macroporous. In the organosilicate compositions of this disclosure, at least 50% of the total pore volume comprises pores with a diameter of 2.0 nanometers or less. In some embodiments at least 50% of the total pore volume comprises pores with a diameter of 0.6-1.3 nanometers.

In some embodiments, the films of this disclosure are prepared from precursor mixtures which are free of porogens. In this context porogens refer to chemical compounds added to the precursor mixture to aid in the formation of the porous structure. Solvents and other components added to the reaction mixture for a different purpose are not considered to be porogens. In other embodiments optional porogen may be added if desired.

Typically a precursor mixture is prepared, coated on a substrate and heated to dry and/or calcine the precursor mixture to form a hydrophobic, amorphous, substantially microporous, organosilicate film.

The precursor mixture may contain a variety of different materials. Among the suitable materials are solvents, at least two hydrolysable silanes, optional porogen, and acids. If the acid used is not an aqueous acid, optional water may also be added.

Typically the precursor mixture contains at least one solvent. The solvent or solvents function to solubilize and dilute the reactants and as a reaction medium for the hydrolysis and condensation reactions that occur in the precursor mixture. The solvent should be able to at least partially solubilize the reactants. Typically the solvent is at least partially miscible with water, since often aqueous reagents such as aqueous acids are used. Suitable solvents include, for example: alcohols such as methanol, ethanol, isopropanol, tert-butanol; ketones such as acetone and methyl ethyl ketone; ethers such as tetrahydrofuran; esters such as ethyl acetate; amides such as dimethylformamide; or mixtures thereof.

The precursor mixture contains at least one hydrolysable silane. Hydrolysable silanes are compounds of the general formula $R_n$—$\{Si(Z)_{4-n}\}_x$ where R is an x-valent hydrocarbon or substituted hydrocarbon group, x is an integer of 1 or greater, Z is a hydrolysable group, and n is an integer of 1, 2 or 3. Suitable hydrolysable groups include alkoxy, halo, acetoxy or amino groups. In some embodiments x is 1, n is 1, the R group is a hydrocarbon group such as an alkyl or aryl group, and Z is an alkoxy. In other embodiments, x is 2, n is 1, R is an alkylene, arylene, aralkalene group, and Z is an alkoxy.

In some embodiments, the precursor mixture contains at least two hydrolysable silanes. In some embodiments, the precursor mixture contains a hydrolysable silane of the general structure $R^1$—$Si(OR^2)_3$ as well as a hydrolysable silane of the general structure $(R^3O)_3Si$—$R^5$—$Si(OR^4)_3$ where $R^1$, $R^2$, $R^3$, and $R^4$, are alkyl or aryl groups, and $R^5$ is an alkylene, arylene or aralkylene group. Examples of suitable hydrolysable silanes include, for example methyl trimethoxy silane, ethyl trimethoxy silane, phenyl trimethoxy silane, 4,4'-bis (triethoxysilyl)-1,1'-biphenyl, and the like. In some embodiments the precursor mixture contains phenyl trimethoxy silane and 4,4'-bis(triethoxysilyl)-1,1'-biphenyl.

The amount of hydrolysable silanes present in the precursor mixture will vary depending upon the nature of the hydrolysable silane or silanes and the desired properties of the formed organosilicate composition. Typically, hydrolysable silanes are present in the range of about 5-25 weight % based upon the total weight of the precursor mixture.

The precursor mixture contains an acid to facilitate the hydrolysis and condensation reactions of the hydrolysable silanes. Any suitable acid can be used as long as it is compatible with the precursor mixture and aids in the hydrolysis reaction. Examples of suitable acids include, for example, organic acids, phosphonium acids, ammonium acids and mineral acids. Organic acids include, for example, carboxylic acids such as acetic acid, sulfonic acids such as alkyl sulfonic acids, phosphonic acids such as alkyl phosphonic acids of the general formula $RP(O)(OH)_2$ where R is an alkyl group and phosphinic acids such as alkyl phosphinic acids of the general formula $R_2P(O)(OH)$ where each R independently is an alkyl group. Phosphonium acids include compounds of the type $R_3PH^+$ where each R independently is a hydrogen or an alkyl or an aryl group. Ammonium acids include compounds of the type $R_3NH^+$ where each R independently is a hydrogen or an alkyl or an aryl group. Mineral acids are inorganic acids that include, for example, hydrochloric acid, nitric acid, sulfuric acid, boric acid, phosphoric acid, hydrofluoric acid and the like. Typically mineral acids are used in their aqueous form, that is to say, the acid is dissolved in water. Generally, due to their availability and ease of use, aqueous mineral acids are used. In some embodiments the acid is aqueous hydrochloric acid.

The precursor mixture may optionally contain at least one porogen. Porogens are materials that facilitate the formation of a porous structure. The porogen does not become covalently attached to the organosilicate composition and typically is removed from the organosilicate composition mixture during or after calcination. Generally the porogen does not contain any functional groups that react with the reactive species in the precursor mixture.

Examples of suitable porogens include polyether surfactants, alkyl ammonium salts, hydrocarbons such as 1,3,5-trimethyl benzene and the like. In some embodiments, the porogen is an ammonium salt such as, for example, an alkyl ammonium salt with a halide counterion. Examples of such salts include tetramethylammonium chloride, tetraethylammonium chloride, tetrapropylammonium chloride, tetra-n-butylammonium chloride, octyltrimethylammonium bromide, decyltrimethylammonium bromide, cetyltrimethylammonium bromide, and the like. One particularly suitable porogen is octyltrimethylammonium bromide. Typically the porogen is present in the precursor mixture in amounts ranging from 1-25 weight %.

Other optional additives can be added to the precursor mixture as long as they do not interfere with the formation of the microporous structure. In particular, especially if an aqueous acid is not used, water may be added to the precursor mixture.

The precursor mixture can be deposited on a substrate to form a layer. The substrate may form a portion of the sensor element or it may be a temporary substrate such that the precursor forms a preformed film of analyte-sensitive organosilicate material. The precursor may be deposited on a substrate using a variety of coating techniques such as, for example spin coating, dip coating, spray coating, roll coating, and printing techniques including, for example, inkjet printing and screen printing. Spin coating is particularly useful.

The substrate may be any suitable substrate upon which it is desirable to prepare an organosilicate layer and which can withstand the calcination step to form the organosilicate layer. Examples of substrates include, for example, metal and metal oxide plates and foils, glass plates, ceramic plates and articles, silicon wafers, polymers capable of withstanding the calcination step such as polyimides and silicones, and the like.

Once the precursor mixture is coated on a substrate it is typically subjected to a heat treatment to dry and calcine the mixture. The heating step may be to a relatively low temperature such as for example 30-100° C. Generally the heating step involves higher temperatures. Typically the coated precursor mixture is heated to a temperature in the range of about 200° C. to about 500° C. In some embodiments the heating step is to about 450° C.

Following the heat treatment additional optional processing steps may be carried out. For example, it may be desirable to treat the organosilicate film with a treating agent. The treating agent can further modify the organosilicate film to make it, for example, more hydrophobic. An example of a suitable treating agent is an organosilane treating agent such as a alkyl disilazane such as hexamethyl disilazane. Such a treatment can be carried out by exposing the layer to vapors of hexamethyl disilazane.

The sensor element includes electrodes as well as the organosilicate layer. With reference to FIGS. 1 and 2, the first electrode 20/120 and second electrode 30/130 can comprise any suitable conductive material. Combinations of different materials (conductive and/or nonconductive) can be used, as different layers or as a mixture, as long as sufficient overall conductivity is provided (e.g., the electrode material comprises a constant resistivity of less than about $10^{-2}$ ohms-meter). Examples of materials that can be used to make the first electrode and/or second electrode include, but are not limited to, organic materials, inorganic materials, metals, alloys, and various mixtures and composites comprising any or all of these materials. In certain embodiments, coated (for example, vapor coated, sputter coated, etc.) metals or metal oxides, or combinations thereof, may be used. Suitable conductive materials include for example aluminum, tin, indium-tin oxide, gold, silver, platinum, palladium, copper, and the like. In one embodiment, both electrodes comprise the same material; in an alternative embodiment, the first and second electrodes comprise different materials.

In various embodiments either or both of the electrodes can be permeable to an organic analyte. Such electrode permeability may be particularly useful in the case of a sensing element which is configured in the general manner of a parallel-plate capacitor as shown in FIG. 1. In such a case, if second electrode 30 is permeable, an organic analyte can enter analyte-responsive organosilicate layer 10 through major surface 13, rather than having to enter the analyte-responsive organosilicate layer 10 by way of edge 15, which might be a slower process. Likewise, if first electrode 20 is permeable, an organic analyte may be able to enter analyte-responsive organosilicate layer 10 through major surface 11 (however, if backing 40 is not permeable to the analyte, it may not be useful to provide first electrode 20 in a permeable configuration).

In various embodiments, an electrode can be analyte-permeable by virtue of being discontinuous. In this context, the term discontinuous does not imply that the electrode comprises units (spots, islands, etc.) that are not in electrical contact with each other. Rather, discontinuous means that within the overall boundaries of the electrode, some areas do not contain conductive material. Such a discontinuous electrode may be microscopically discontinuous. For example, an electrode can be formed by the deposition (e.g., by coating, ink jet printing, etc.) of a sol comprising particles (e.g. nanoparticles) of a conductive material. In such a case, the electrode comprises conductive particles that are in sufficient contact to ensure that the electrode is conductive, but with sufficient spaces in between the particles to render the electrode permeable to an organic analyte. In other embodiments, an electrode can comprise a macroscopically discontinuous structure. For example, if a conductive material comprises vapor coated metal (which is typically impermeable), the conductive metal can be deposited in a pattern (for example, in a grid pattern, or in a "comb" pattern) rather than as a continuous layer.

With reference to FIGS. 1 and 2, an electrically accessible area 25/125 of first electrode 20/120, and an electrically accessible area 35/135 of second electrode 30/130, are provided such that it is possible to connect an operating circuit 28/128 to the sensing element via these areas. Such electrically accessible areas can be provided in any convenient location. For example, such electrically accessible areas are shown on an edge of the electrodes in the exemplary illustrations of FIGS. 1 and 2, and are shown on a major surface (123 and 133) of the electrodes in the exemplary illustration of FIG. 3. In one embodiment, a connecting device (e.g. a contact pad or tab) 22/122 is positioned in contact with (e.g. attached to) the accessible area of the first electrode 20, such that electrical connection can be made (for example via attachment of wires 24/124) between sensing element 1/101 and an operating circuit 28/128. A similar connecting device 32/132 can be likewise positioned in contact with the accessible area of the second electrode 30.

In one embodiment, a sensing element 1 can be produced which is configured in the general manner of a parallel-plate capacitor as shown in an exemplary manner in the cross sectional view of FIG. 1. In such a configuration, the sensing element comprises two generally planar, parallel, opposing electrodes, with the analyte-responsive organosilicate layer being present in between the electrodes and preventing direct electrical contact between the two electrodes.

In an exemplary process for making such a sensing element, a backing 40 is provided (which may be a continuous slab, layer or film of material) that is in proximity to at least one of the electrodes and that may serve to provide physical strength and integrity to the finished sensing element. Any suitable material may be used, including glass, ceramic, plastic, etc. In large scale production, a polymeric film (such as polyester) may be used. In some embodiments, the backing is an analyte-permeable material (for example, silicone rubber, a microporous membrane, etc.).

In one embodiment, a conductive layer that serves as first electrode 20 is provided on backing 40. The conductive layer may comprise any of the materials mentioned above, including blends or mixtures of conductive and nonconductive materials, and may be deposited by any suitable method, including but not limited to spin coating, dip coating, screen printing, transfer coating, sputter-coating, physical vapor deposition, chemical vapor deposition, or a combination of two or more of such methods. In an alternate embodiment, the conductive layer may be provided by placing a premade film (e.g. a metal foil, conductive tape, etc.) atop backing 40. This first electrode 20 may be provided as a continuous layer or as a discontinuous layer, as previously described.

In one embodiment, the conductive layer is provided such that a first surface 21 of electrode 20 is in proximity to, and/or in contact with, at least a portion of the first surface 41 of backing 40. In an alternative embodiment, an optional layer is present between at least a part of first surface 21 of electrode 20, and first surface 41 of backing 40. Such an optional layer may be used for any purpose (such as improving the bond between first electrode 20 and backing 40), as long as the layer does not interfere with the functioning of the sensing element 1.

In producing sensing element 1, an analyte-responsive organosilicate layer 10 is also provided. In one embodiment, the analyte-responsive organosilicate layer 10 is provided such that first major surface 11 of layer 10 is in direct contact with at least a portion of the second surface 23 of first electrode 20 (leaving at least a portion of first electrode 20 accessible for connection to an operating circuit).

In one embodiment, the analyte-responsive organosilicate material is placed in proximity to the first electrode by a coating process, for example, including but not limited to spin coating, dip coating, printing techniques, and the like as described above. In certain embodiments, the dielectric material is deposited in such a manner as to minimize the presence of defects, pinholes, etc., that might serve to compromise the performance of the sensing element.

An analyte-responsive organosilicate layer 10 can also be provided by other methods. For example, a preformed film of analyte-responsive organosilicate material can be placed upon the second surface of the first electrode. In an alternative embodiment, the analyte-responsive organosilicate material can be provided in particulate form (e.g. as a powder, as a suspension, or as a sol) and deposited in such a form onto a first electrode so as to form a particulate coating. If desired, such a material can be consolidated so as to form a continuous matrix of analyte-responsive organosilicate material.

In various embodiments, a second electrode 30 can be formed by placing a second conductive layer in proximity to the analyte-responsive organosilicate layer 10. The second electrode 30 may comprise conductive materials as described above, and may be deposited according to methods described above. In certain embodiments (particularly in the case in which backing 40 is impermeable to an analyte), the second electrode may comprise a discontinuous structure (again as previously described) so as to be permeable to an organic analyte.

With reference to FIG. 1, an optional protective cover or barrier layer 50 can be provided in proximity to at least one of the electrodes. In one embodiment, cover layer 50 can be placed atop second electrode 30 (leaving an area of second electrode 30 accessible for electrical contact). Any such cover layer 50 should not significantly interfere with the functioning of sensing element 1. For example, if the sensing element is configured such that an analyte of interest must pass through cover layer 50 in order to reach the analyte-responsive organosilicate layer 10, the cover layer should be sufficiently permeable to the analyte.

Cover layer 50 may be deposited by any method known in the art, including coating (e.g. spin coating, dip coating, solvent coating, vapor coating, transfer coating, screen printing, flexographic printing, and the like). In an alternate embodiment, cover layer 50 can comprise a premade layer (e.g. a film or tape) that is placed upon second electrode 30. In one embodiment, cover layer 50 is provided such that first surface 51 of cover layer 50 is in direct contact with at least a portion of second surface 33 of second electrode 30. The second surface of the cover layer may be the outermost surface of the sensing element, or may itself receive additional coatings or layers if desired.

In one embodiment, the second surface 23 of first electrode 20 and first major surface 11 of the analyte-responsive organosilicate layer 10 are in direct contact, with no interposing layer(s) therebetween. Likewise in one embodiment, the first surface 31 of second electrode 30 and second major surface 13 of the analyte-responsive organosilicate layer 10 are in direct contact, with no interposing layer(s) therebetween. Such embodiments are pictured in FIG. 1. However, it is also contemplated that other, optional layers may be present between the first electrode 20 and the analyte-responsive organosilicate layer 10, and/or between the second electrode 30 and the analyte-responsive organosilicate layer 10. In such a case, either or both of the electrodes may not be in direct contact with some or all of a surface of the analyte-responsive organosilicate material. For example, a tie layer or layers may be used to improve the bonding between an electrode and the analyte-responsive organosilicate layer. Or, a passivation layer or layers (for example, a layer of silicon dioxide) may be placed in between a surface of the analyte-responsive organosilicate layer and an electrode surface, in order to minimize the possibility of arcing between the electrodes. In some embodiments, multiple such optional layers may be used; alternatively a single layer may serve multiple functions. Any such optional layer or layers such as the aforementioned tie layers, passivation layers, protective layers, cover layers, etc., may be used, for whatever purpose, as long as they do not significantly interfere with the desired functioning of the sensing element. For example, an optional layer should be sufficiently permeable to an analyte of interest if the sensing element is configured such that the analyte must pass through the optional layer in order to reach the analyte-responsive organosilicate layer 10.

In general, the edges of the various layers can be aligned flush with each other (as depicted in the exemplary embodiment of FIG. 1). Alternatively, various layers may overlap other layers, and/or the edges of certain layers may be recessed relative to other layers.

In the deposition of the analyte-responsive organosilicate material atop first electrode 20, an electrically accessible area 25 should be provided on first electrode 20, to enable electrical contact between the electrode and an operating circuit. Similarly, if a cover layer is placed atop second electrode 30, an electrically accessible area 35 should be similarly provided. Such electrically accessible areas can be provided in any convenient location. In one embodiment, a connecting device (e.g. a contact pad, tab, or the like) 22 may be placed in electrical contact with accessible area 25 of first electrode 20. Similarly, a connecting device 32 may be placed likewise in contact with accessible area 35 of second electrode 30.

Figure 2A:
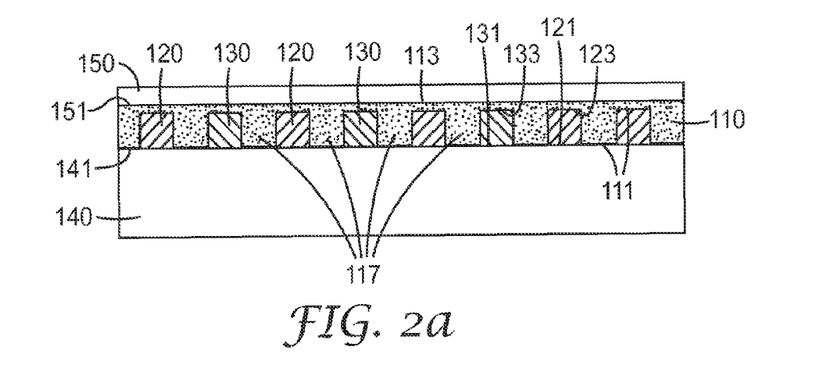
FIG. 2a is a cross sectional view of the exemplary sensing element of FIG. 2, taken along the line marked "2a" in FIG. 2.
Figure 3:
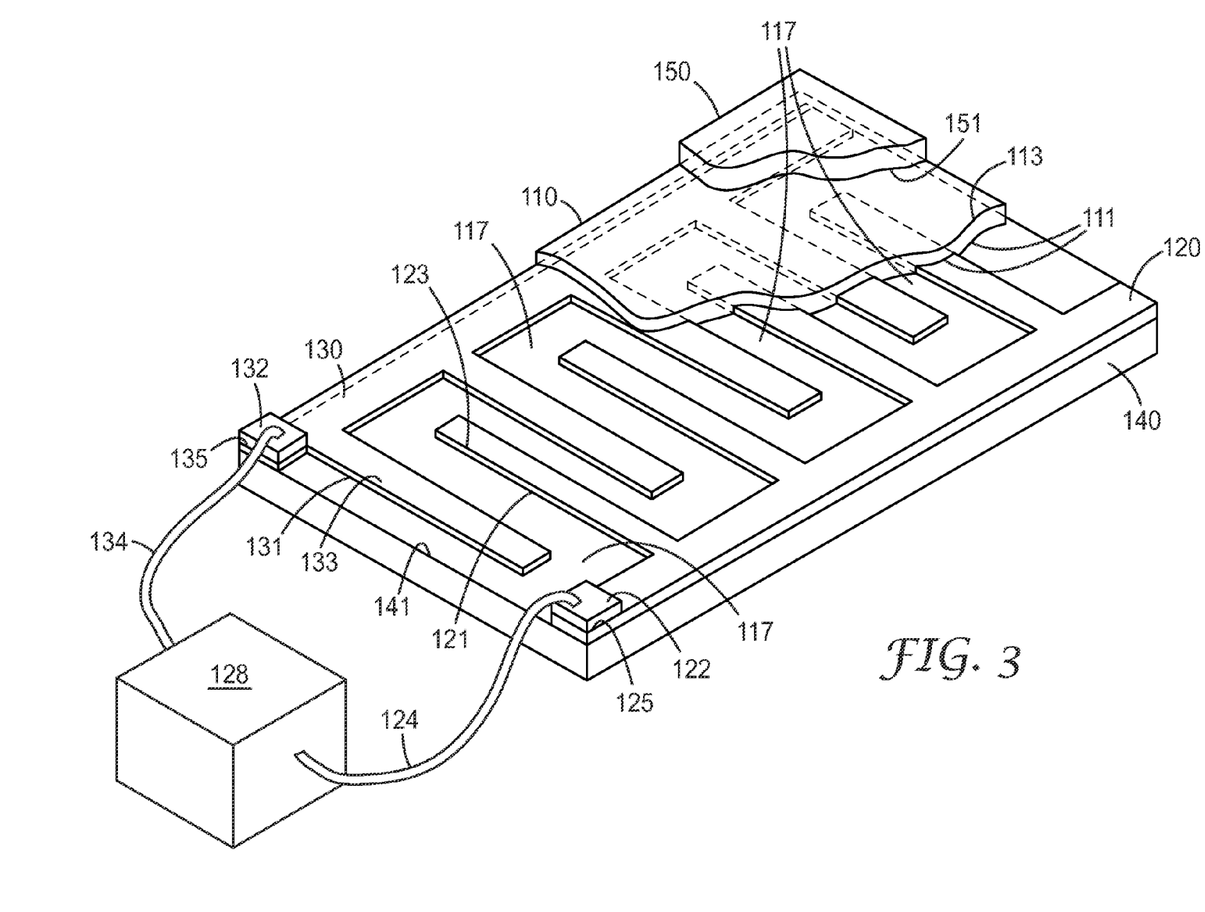
FIG. 3 is a perspective view of an exemplary sensing element in an interdigitated configuration.

In another embodiment, a sensing element can be produced that is configured in the general manner of an interdigitated capacitor. Exemplary embodiments of interdigitated sensing elements are shown in the top view of FIG. 2, in the cross-sectional view of FIG. 2a (taken along the line marked "2a" in FIG. 2), and in the perspective view of FIG. 3. In this context, the term interdigitated encompasses any arrangement comprising at least two electrodes present in an interdigitated configuration. Such configurations include interdigitated comb patterns (such as depicted in FIGS. 2, 2a and 3), as well as interdigitated spiral or serpentine patterns as are well known in the art. All of these designs have the common characteristic that (at least) two electrodes are present in a largely coplanar interdigitated arrangement with an analyte-responsive organosilicate layer present in proximity to the electrodes such that when an electric field is established between the electrodes, an analyte-responsive organosilicate material contained in the layer is capable of interacting with the electric field. The analyte-responsive organosilicate layer/material may be provided between the electrodes (i.e. in the plane of the two electrodes and interposed in the closest linear path between any two points of approach of the first and second electrodes). Alternatively, the analyte-responsive organosilicate layer/material may be provided such that, while not coplanar with the electrodes, the analyte-responsive organosilicate material is exposed at least to the fringing electric field that is established between adjacent sections of the two electrodes. In still another alternate embodiment, the analyte-responsive organosilicate layer may be provided in both locations.

Interdigitated electrodes can be provided by the deposition of conductive material in two interdigitated patterns by any of the methods (e.g. masked vapor deposition, screen-printing, ink-jet printing) that are well known for patterned deposition of materials. The particular geometric/dimensional properties of the electrode patterns (spacing, height, length etc.) may be designed as desired.

In one embodiment, interdigitated electrodes are provided on a backing 140 which may be comprised of materials described above. First electrode 120 and second electrode 130 are typically provided on the same backing 140. In one embodiment (shown in FIGS. 2, 2a and 3), first surface 121 of first electrode 120, and first surface 131 of second electrode 130, are both in direct contact with at least some portion of the first surface 141 of backing 140. In an alternative embodiment (not pictured), an optional layer or layers can be present between the electrode 120 and/or 130 and the backing 140, similar to the optional layers described above, and subject to the same issues and constraints.

As illustrated in the exemplary embodiments of FIGS. 2, 2a, and 3, the patterned deposition of first electrode 120 and second electrode 130 may leave an area of surface 141 of backing 140, (or, of the surface of any optional layer thereupon) exposed. An analyte-responsive organosilicate layer can then be deposited onto backing 140, via similar methods to those described above with reference to sensing elements of a parallel-plate type. The deposited analyte-responsive organosilicate material will thus fill the spaces between the two electrodes (e.g. spaces 117 depicted in FIGS. 2, 2a, and 3). Thus, in this embodiment a first surface 111 of the analyte-responsive organosilicate layer 110 will be in direct contact with at least a portion of surface 141 of backing 140. The deposition process may also cause the analyte-responsive organosilicate layer 110 to cover, and be in contact with, second surface 123 of the first electrode, and second surface 133 of the second electrode, as depicted in FIGS. 2a and 3 (unless the deposition is performed selectively, e.g. with one or both of the electrodes masked). Thus, in various embodiments, the first surface 111 of analyte-responsive organosilicate layer 110 is in direct contact with second surface 123 of first electrode 120, and/or with second surface 133 of second electrode 130.

In alternative embodiments, an optional layer (not shown in FIGS. 2, 2a, or 3) may be provided atop the second surface 123 of first electrode 120, and/or atop the second surface 133 of first electrode 130. (In this embodiment, direct contact between first surface 111 of analyte-responsive organosilicate layer 110 and second surface 123 of first electrode 120, and/or second surface 133 of second electrode 130, may not occur). Such an optional layer may serve similar purposes (protective, etc.) to those described earlier. However, in an interdigitated type sensing element, an optional layer atop one or both electrodes may not necessarily need to be permeable to the analyte since the analyte may not need to penetrate through the an optional layer to reach areas 117 of the analyte-responsive organosilicate layer 110.

In one embodiment, an optional cover layer 150 (which may serve as a protective layer, insulating layer, decorative layer, etc.) is provided such that first surface 151 of cover layer 150 may be deposited atop the second surface 113 of the analyte-responsive organosilicate layer 110. Any such cover layer should not significantly interfere with the functioning of the sensing element (e.g., it should be sufficiently permeable to an analyte of interest). This cover layer may comprise a coating deposited by any known coating process (e.g. spin coating, dip coating, solvent coating, vapor coating, transfer coating, screen printing, flexographic printing, and the like). In an alternate embodiment, cover layer 150 can comprise a premade layer (e.g. a film or tape) that is placed atop second surface 113 of layer 110.

In the deposition of the analyte-responsive organosilicate material (and of any optional cover layer), an electrically accessible area 125 should be provided on first electrode 120, and an accessible area 135 on second electrode 130, to allow electrical contact between each electrode and an operating circuit. Such electrically accessible areas can be provided in any convenient location. For example, such electrically accessible areas 125 and 135 are shown on an edge of an electrode in the exemplary illustration of FIG. 2, and are shown on surfaces 123 and 133 of an electrode in the exemplary illustration of FIG. 3.

In one embodiment, a connecting device (e.g. a contact pad, tab, or the like) 122 may be placed in electrical contact with accessible area 125 of first electrode 120. Similarly, a connecting device 132 may be placed likewise in contact with accessible area 135 of second electrode 130.

Figure 4:
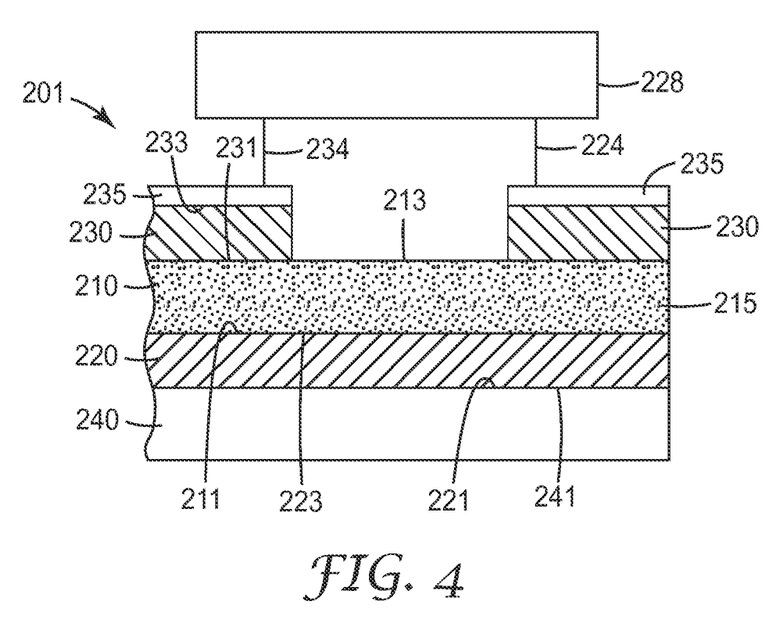
FIG. 4 is a side view of an exemplary sensing element containing multiple parallel-plate capacitors connected in series.

For ease of manufacturing, it may be useful to prepare a device containing multiple parallel-plate capacitors connected in series. An example of such an embodiment is shown in FIG. 4.

In producing sensing element 201, an analyte-responsive organosilicate layer 210 is also provided. In one embodiment, the analyte-responsive organosilicate layer 210 is provided such that first major surface 211 of layer 210 is in direct contact with at least a portion of the second surface 223 of first electrode 220.

In one embodiment, the analyte-responsive organosilicate material is placed in proximity to the first electrode by a coating process, for example, including but not limited to spin coating, dip coating, printing techniques, and the like as described above. In certain embodiments, the material is deposited in such a manner as to minimize the presence of defects, pinholes, etc., that might serve to compromise the performance of the sensing element.

An analyte-responsive organosilicate layer 210 can also be provided by other methods. For example, a preformed film of analyte-responsive organosilicate material can be placed upon the second surface of the first electrode.

In various embodiments, second electrodes 230 can be formed by placing a discontinuous second conductive layer in proximity to the analyte-responsive organosilicate layer 210. The second electrodes 230 may comprise conductive materials as described above, and may be deposited according to methods described above.

In one embodiment, the second surface 223 of first electrode 220 and first major surface 211 of the analyte-responsive organosilicate layer 210 are in direct contact, with no interposing layer(s) therebetween. Likewise in one embodiment, the first surface 231 of second electrode 230 and second major surface 213 of the analyte-responsive organosilicate layer 210 are in direct contact, with no interposing layer(s) therebetween. Such embodiments are pictured in FIG. 4. However, it is also contemplated that other, optional layers may be present between the first electrode 220 and the analyte-responsive organosilicate layer 210, and/or between the second electrode 230 and the analyte-responsive organosilicate layer 210. In such a case, either or both of the electrodes may not be in direct contact with some or all of a surface of the analyte-responsive organosilicate material. For example, a tie layer or layers may be used to improve the bonding between an electrode and the analyte-responsive organosilicate layer. Or, a passivation layer or layers (for example, a layer of silicon dioxide) may be placed in between a surface of the analyte-responsive organosilicate layer and an electrode surface, in order to minimize the possibility of arcing between the electrodes. In some embodiments, multiple such optional layers may be used; alternatively a single layer may serve multiple functions. Any such optional layer or layers such as the aforementioned tie layers, passivation layers, protective layers, cover layers, etc., may be used, for whatever purpose, as long as they do not significantly interfere with the desired functioning of the sensing element. For example, an optional layer should be sufficiently permeable to an analyte of interest if the sensing element is configured such that the analyte must pass through the optional layer in order to reach the analyte-responsive organosilicate layer 210.

In general, the edges of the various layers can be aligned flush with each other (as depicted in the exemplary embodiment of FIG. 4). Alternatively, various layers may overlap other layers, and/or the edges of certain layers may be recessed relative to other layers.

In the deposition of the second electrodes 230, an electrically accessible area 235 should be provided. Such electrically accessible areas can be provided in any convenient location. In one embodiment, a connecting device (e.g. a contact pad, tab, or the like) 235 may be placed in electrical contact with accessible area of second electrodes 230. The contact between electrode 230 and electrically accessible area 235, interface 233, may be direct contact or there may be layers in between.

In some embodiments, the conductive layer is provided such that a first surface 221 of electrode 220 is in proximity to, and/or in contact with, at least a portion of the first surface 241 of optional backing 240. Backing 240 may be the same as the backings 40 and 140 described previously. In an alternative embodiment, an optional layer is present between at least a part of first surface 221 of electrode 220, and first surface 241 of backing 240. Such an optional layer may be used for any purpose (such as improving the bond between first electrode 220 and backing 240), as long as the layer does not interfere with the functioning of the sensing element 201.

In various embodiments either or both of the electrodes can be permeable to an organic analyte. Such electrode permeability may be particularly useful in the case of a sensing element which is configured in the general manner of a parallel-plate capacitor as shown in FIG. 4. In such a case, if second electrodes 230 are permeable, or even if they are not, an organic analyte can enter analyte-responsive organosilicate layer 210 through major surface 213, rather than having to enter the analyte-responsive organosilicate layer 210 by way of edge 215, which might be a slower process. Likewise, if first electrode 220 is permeable, an organic analyte may be able to enter analyte-responsive organosilicate layer 210 through major surface 211 (however, if backing 240 is not permeable to the analyte, it may not be useful to provide first electrode 220 in a permeable configuration).

Upon absorption of sufficient analyte by the analyte-responsive organosilicate layer, a detectable change in an electrical property associated with the sensing element (including but not limited to, capacitance, impedance, admittance, current, or resistance) may occur. Such a detectable change may be detected by an operating circuit 28/128/228 that is in electrical communication with the first and second electrodes. In this context, "operating circuit" refers generally to an electrical apparatus that can be used to apply a voltage to the first electrode and the second electrode (thus imparting a charge differential to the electrodes), and/or to monitor an electrical property of the sensing element, wherein the electrical property may change in response to the presence of an organic analyte. In various embodiments, the operating circuit may monitor any or a combination of inductance, capacitance, voltage, resistance, conductance, current, impedance, phase angle, loss factor, or dissipation.

Such an operating circuit may comprise a single apparatus which both applies voltage to the electrodes, and monitors an electrical property. In an alternative embodiment, such an operating circuit may comprise two separate apparatuses, one to provide voltage, and one to monitor the signal. An operating circuit may be connected to first electrode 20/120 and to second electrode 30/130 by wires 24/124 and 34/134. In an alternative embodiment, an operating circuit may be provided in direct contact with the first and/or the second electrode, either via connecting devices 22/122 and 32/132, or by contacting some portion of the operating circuit directly to an electrically accessible area of each electrode. For example, an operating circuit can be provided that resides on a circuit board or a flexible circuit (either of which can also serve as backing 40/140). A first electrode can then be deposited directly onto circuit board/backing 40 such that it is in direct contact with a portion of the operating circuit. In another alternative embodiment (FIG. 4) second electrodes 230 are connected to the operating circuit via connecting devices 235 by wires 224 and 234. This arrangement provides 2 sensing elements operating in series.

An operating circuit 28/128/228 may include, for example, a power supply (which may comprise a battery or a hardwired power source; alternatively, power may be provided indirectly via, for example, charging of an RFID circuit that is built into the operating circuit). An operating circuit 28/128/228 may also include one or more microprocessors configured to control the charging of the electrodes and/or to monitor changes in one or more electrical properties of a charged sensing electrode pair. Also present may be analog-to-digital converters, memory devices for storing data derived from the sensing element, software for operating the sensing element, components that provide data logging and/or one- or two-way telemetry capability, and so on.

A sensing element such as herein disclosed can be used to detect and/or monitor (whether qualitatively or quantitatively) the presence of an organic analyte or analytes. Such analytes can include, but are not limited to, hydrocarbons, fluorocarbons, alkanes, cycloalkanes, aromatic compounds, alcohols, ethers, esters, ketones, halocarbons, amines, organic acids, cyanates, nitrates, and nitriles, for example n-octane, cyclohexane, methyl ethyl ketone, acetone, ethyl acetate, carbon disulfide, carbon tetrachloride, benzene, styrene, toluene, xylenes, methyl chloroform, tetrahydrofuran, methanol, ethanol, isopropyl alcohol, n-butyl alcohol, t-butyl alcohol, 2-ethoxyethanol, acetic acid, 2-aminopyridine, ethylene glycol monomethyl ether, toluene-2,4-diisocyanate, nitromethane, and acetonitrile and the like. Analytes can be relatively nonpolar organic molecules or relatively polar organic molecules. Analytes can be so-called vapors; i.e. molecules that are capable of forming a solid or liquid under the ambient conditions of temperature and pressure that the analyte is experiencing (e.g. toluene, acetone, heptane, etc.). Analytes can be so-called gases; i.e. molecules that are not normally capable of forming a liquid or solid under ambient conditions (although such molecules may still comprise a more highly condensed state in the internal pores of the analyte-responsive organosilicate material, as discussed above). Such gases may include methane, ethane, and the like. Mixtures of organic analyte molecules may in some circumstances be detected.

EXAMPLES

These examples are merely for illustrative purposes only and are not meant to be limiting on the scope of the appended claims. All parts, percentages, ratios, etc. in the examples and the rest of the specification are by weight, unless noted otherwise. Solvents and other reagents used were obtained from Sigma-Aldrich Chemical Company; Milwaukee, Wis. unless otherwise noted.

| Table of Abbreviations | |
|---|---|
| Abbreviation or Trade Designation | Description |
| OTAB | octyltrimethylammonium bromide |
| BTSBP | 4,4'-bis(triethoxysilyl)-1,1'-biphenyl |
| PTMS | phenyl(trimethoxy)silane |
| HMDS | Hexamethyldisilazane |
| Silicon Wafers | P<100>, 0-100 $\Omega \cdot$ cm 500 ± 20 µm thickness silicon wafers, commercially available from University Wafers, cleaned with acetone prior to use. |
| Nanosilver Ink | Nanosilver Ink commercially available from Advanced Nanoproducts as DGP-40LT-25C, Lot ANP-3M-071031. |

Test Methods
Determination of Pore Sizes

Material identical to that of Example 1 was prepared for nitrogen adsorption measurements by coating the mixture on a 100 mm diameter Silicon Wafer. The wafer was coated repeatedly using the spin-coating method and subsequently calcined as described in the Example. The film was removed from the silicon wafer and used for nitrogen adsorption measurements. Total pore volume was measured by nitrogen adsorption using a gas adsorption analyzer available under the trade designation "QUANTACHROME AUTOSORB IC" (Quantachrome Instruments, Boynton Beach, Fla.) operated according to the manufacturer's directions using a 74 point micro pore analysis.

X-ray Scattering

Samples were tested for X-ray scattering to determine the amorphous nature of the sample. Reflection geometry data were collected in the form of a survey scan by use of a Philips vertical diffractometer, copper $K_\alpha$ radiation, and proportional detector registry of the scattered radiation. The diffractometer was fitted with variable incident beam slits, fixed diffracted beam slits, and graphite diffracted beam monochromator. The survey scan was conducted from 5 to 80 degrees (2θ) using a 0.04 degree step size and 4 second dwell time. X-ray generator settings of 45 kV and 35 mA were employed. Additional reflection geometry low angle data were collected by use of a Huber 4-circle diffractometer, copper $K_\alpha$ radiation, and scintillation detector registry of the scattered radiation. The incident beam was collimated to a 700 μm pinhole and nickel filtered. Scan was conducted from 0.5 to 15 degrees (2θ) using a 0.01 degree step interval and 60 second dwell time. X-ray generator settings of 40 kV and 20 mA were employed.

Capacitance Response Testing

Figure 5:
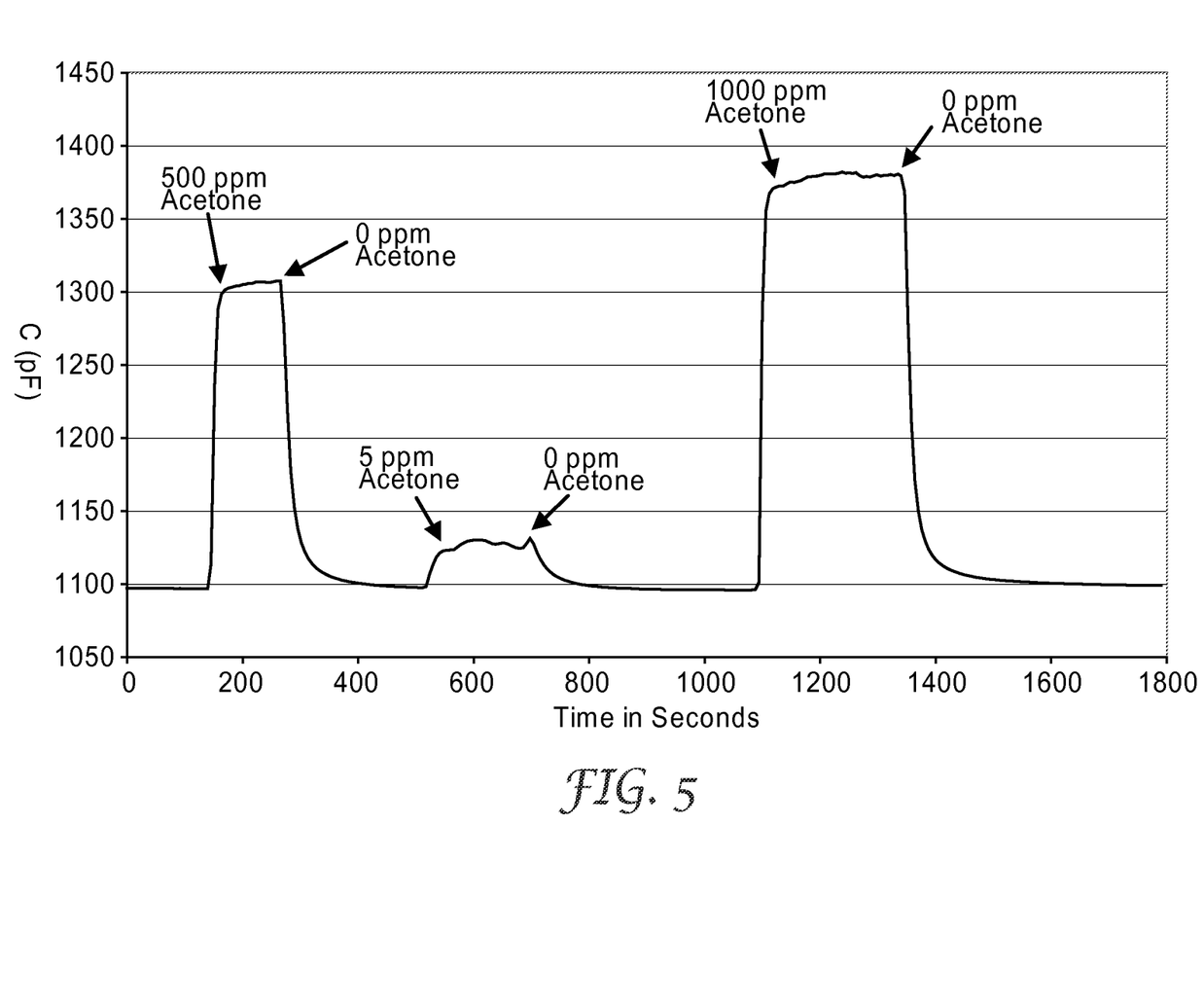
FIG. 5 is a plot of the measured capacitance of an exemplary sensing element of a sensing element with multiple parallel-plate capacitors connected in series, as a function of time of exposure to various levels of an organic analyte.

A simple flow-through delivery system was used to deliver known concentrations of acetone to the sample for measurement. Teflon tubing was used throughout the delivery system. The exposure concentrations were generated by metering acetone flow into the evaporation flask by means of kd Scientific 200 Series syringe pump and 1 ml Hamilton 1000 Series Gastight syringe. The evaporation flask contained 42.5 mm in diameter #1 type filter paper to enhance the evaporation process in conjunction with stream of nitrogen gas controlled by Matheson gas flowmeter. The calculations for the set points of a syringe pump and the flow rate for the nitrogen (to get the desire concentration of acetone vapors) were done using the textbook "Gas Mixtures: Preparation and Control" (Gary O. Nelson, Lewis Publishers, 1992). The concentration of acetone in the gaseous stream was monitored with infrared spectrometer (available under the designation Miran Sapphire from ThermoElectron of Waltham, Mass.). The gaseous acetone stream was introduced into a sample chamber (held at controlled temperature) containing the sample. The first and second electrodes of the sample were connected to an operating circuit that comprised an LCR meter (available under the designation Instek Model 821 LCR meter from Instek America, Corp. Chino, Calif.) using spring loaded probes. The changes in capacitance (in picoFarads) of the sample were monitored at frequency of 1 kHz and specific time intervals during the entire course of the vapor test (as shown in FIG. 5).

Example 1

A substrate was prepared by vapor depositing a 100 nanometers thick layer of aluminum onto a 25×25 mm² section of a glass plate. The aluminum was coated by vapor deposition with a 20 nanometer thick layer of silicon oxide.

A coating solution was prepared by combining in a polyethylene bottle in order: OTAB (0.124 gram), ethanol (2.106 grams), BTSBP (0.392 gram), PTMS (0.102 gram), and 0.1 M HCl (aq) (0.205 gram).

A sample of this coating solution was used to prepare a sample to determine the pore size. Testing using the pore size determination test shown in the Test Methods above was carried out. The results of the test demonstrated that 75% of the total pore volume contained pores with a pore diameter of 2.0 nanometers or less, and 70% of the total pore volume contained pores with a diameter of 1.5 nanometers or less.

A sample of this coating solution was used to prepare a sample for X-ray Scattering analysis. After 115 minutes, the coating solution was spin-coated onto a Silicon Wafer using a Headway Research EC101 DT-R790 spin-coater using a 2 centimeter diameter chuck. The section was flooded with several drops of solution prior to spinning. The spin-coating was performed at 1000 rpm for 60 seconds. The coated sample was calcined in air in a furnace to a temperature of 450° C. X-ray Scattering analysis was carried out using the test method described above. The results of the test demonstrated no evidence for the presence of structural order. The low and wide angle data obtained were essentially featureless.

An additional portion of the coating solution was used to prepare a test electrode. After 115 minutes, the coating solution was spin-coated onto the substrate described above using a Headway Research EC101 DT-R790 spin-coater using a 2 centimeter diameter chuck. The section was flooded with several drops of solution prior to spinning. The spin-coating was performed at 1000 rpm for 60 seconds. The coated sample was calcined in air in a furnace to a temperature of 450° C. The sample coating was post-treated by exposure to HMDS by placing it into a polystyrene petri dish with a reservoir of HMDS (1-2 milliliters). The petri dish was covered, and the sample was allowed to react with HMDS vapor for 24 hours. Permeable electrodes were painted onto the surface of the sample using Nanosilver Ink This resulting construction was heated in an oven in air at 150° C. for 1 hour. Capacitance response testing was carried out as described in the Test Method above. The results are shown in FIG. 5.

What is claimed is:

1. A sensing element for sensing an organic chemical analyte, comprising:
    a first electrode and a second electrode; and
    a substantially microporous, amorphous, hydrophobic, analyte-responsive organosilicate material disposed at least in proximity to the first and second electrodes, wherein the substantially microporous, amorphous, hydrophobic, analyte-responsive organosilicate material comprises micropores which define a pore volume.

2. The sensing element of claim 1 wherein the substantially microporous, amorphous, hydrophobic, analyte-responsive organosilicate material adsorbs water into less than 50% of the available pore volume at a relative humidity of 50% at equilibrium.

3. The sensing element of claim 1 wherein the substantially microporous, amorphous, hydrophobic, analyte-responsive organosilicate material does not display a detectable X-ray diffraction pattern when scanned from 0.5 to 80 degrees (2θ).

4. The sensing element of claim 1 wherein at least 50% of the total pore volume comprises pores with a diameter of 2.0 nanometers or less.

5. The sensing element of claim 1 wherein at least 50% of the total pore volume comprises pores with a diameter of 0.6-1.3 nanometers.

6. The sensing element of claim 1 in which at least one of the electrodes is permeable to an organic chemical analyte.

7. The sensing element of claim 6 wherein the permeable electrode comprises a discontinuous layer of conductive material.

8. The sensing element of claim 6 wherein the permeable electrode comprises a patterned layer of conductive material.

9. The sensing element of claim 1 wherein the sensing element comprises a parallel-plate capacitor configuration.

10. The sensing element of claim 1 wherein the sensing element comprises an interdigitated capacitor configuration.

11. The sensing element of claim 1 wherein the sensing element comprises a multiple parallel-plate connected in series capacitor configuration.

12. The sensing element of claim 1 wherein the sensing element comprises a backing in proximity to at least one of the electrodes.

13. The sensing element of claim 1 wherein the sensing element comprises a cover layer in proximity to at least one of the electrodes.

14. The sensing element of claim 13 wherein the cover layer is permeable to an organic chemical analyte.

* * * * *

UNITED STATES PATENT AND TRADEMARK OFFICE
CERTIFICATE OF CORRECTION

| | |
|---|---|
| PATENT NO. | : 8,409,511 B2 |
| APPLICATION NO. | : 13/141585 |
| DATED | : April 2, 2013 |
| INVENTOR(S) | : J. Christopher Thomas et al. |

It is certified that error appears in the above-identified patent and that said Letters Patent is hereby corrected as shown below:

Column 1 – Title Page, Item (54), Line 2, – and
Column 1 – in the Specification, Line 2 – Title
Delete "ORGANISILICATE" and insert -- ORGANOSILICATE --, therefor.

Column 2 – Title Page – Other Publications
Line 2, Delete "proprties" and insert -- properties --, therefor.

Column 2 – Title Page 2 – U.S. Patent Documents
Line 17, Delete "Weigel" and insert -- MacDougall, et al. --, therefor.

Column 2 – Title Page 2 – Other Publications
Line 4, Delete "t eintersection" and insert -- the intersection --, therefor.

In the Specification

Column 6
Line 66, Delete "aralkalene" and insert -- aralkylene --, therefor.

Column 9
Line 15, Delete "ink jet" and insert -- ink-jet --, therefor.

Column 18
Line 17, Delete "Ink" and insert -- Ink. --, therefor.

Signed and Sealed this
Twenty-ninth Day of April, 2014

Michelle K. Lee
*Deputy Director of the United States Patent and Trademark Office*